（12) United States Patent
Gold et al.

(10) Patent No.: US 10,702,272 B2
(45) Date of Patent: Jul. 7, 2020

(54) HANDLELESS CLAMPING DEVICE

(71) Applicant: INTUITIVE SURGICAL OPERATIONS, INC., Sunnyvale, CA (US)

(72) Inventors: Adam Gold, Scottsdale, AZ (US); David J. Danitz, San Jose, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 5 days.

(21) Appl. No.: 15/699,883

(22) Filed: Sep. 8, 2017

(65) Prior Publication Data

US 2017/0367703 A1    Dec. 28, 2017

Related U.S. Application Data

(60) Division of application No. 13/942,390, filed on Jul. 15, 2013, now Pat. No. 9,782,174, which is a
(Continued)

(51) Int. Cl.
*A61B 17/08* (2006.01)
*A61B 17/122* (2006.01)
(Continued)

(52) U.S. Cl.
CPC ............ *A61B 17/08* (2013.01); *A61B 17/122* (2013.01); *A61B 17/1285* (2013.01); *A61B 2017/00473* (2013.01)

(58) Field of Classification Search
CPC ..... A61B 17/08; A61B 17/122; A61B 17/128; A61B 17/1285; A61B 5/6838; A61B 5/6884
See application file for complete search history.

(56) References Cited

U.S. PATENT DOCUMENTS 2,400,142 A    5/1946  Tinnerman
2,549,229 A    4/1951  Ottoson
(Continued)

FOREIGN PATENT DOCUMENTS

CA    618821 A    4/1961
DE    19719090 A1    11/1998
(Continued)

OTHER PUBLICATIONS

International Search Report for Application No. PCT/US03/09035, dated Apr. 23, 2004, 3 pages.
(Continued)

*Primary Examiner* — Christopher D. Prone
(74) *Attorney, Agent, or Firm* — Haynes and Boone, LLP

(57) ABSTRACT

A method comprises rotating a first rotating element to cause rotation of a second rotating element and restricting, by an elongate slot of a first body portion and a pin affixed to a second body portion, a range of rotational motion of first and second jaw portions of a medical instrument. The first jaw portion is coupled to the second jaw portion by the first body portion and the second body portion. The rotation of the second rotating element causes translation of a first actuation element along a rotational axis of the second rotating element. The translation of the first actuation element causes pivotal motion of the first jaw portion towards the second jaw portion about a single pivot pin. The elongate slot of the first body portion and the pin affixed to the second body portion are positioned between the second rotating element and the single pivot pin.

20 Claims, 14 Drawing Sheets

Related U.S. Application Data continuation of application No. 12/335,431, filed on Dec. 15, 2008, now Pat. No. 8,506,590, which is a division of application No. 10/397,915, filed on Mar. 25, 2003, now Pat. No. 7,588,585.

(60) Provisional application No. 60/368,074, filed on Mar. 26, 2002.

(51) Int. Cl.
*A61B 17/128* (2006.01)
*A61B 17/00* (2006.01)

(56) References Cited

U.S. PATENT DOCUMENTS

| | | | |
|---|---|---|---|
| 2,592,484 | A | 4/1952 | Smith |
| 3,136,040 | A | 6/1964 | Bauer et al. |
| 3,503,397 | A | 3/1970 | Thomas et al. |
| 3,602,989 | A | 9/1971 | Averitt |
| 3,664,621 | A | 5/1972 | Savoie, Jr. |
| 3,797,498 | A | 3/1974 | Walsh et al. |
| 4,009,899 | A | 3/1977 | Johnson |
| 4,248,233 | A | 2/1981 | Von Zeppelin |
| 4,424,811 | A | 1/1984 | Groot |
| 4,443,196 | A * | 4/1984 | Rico ............... A61C 3/14 433/158 |
| 4,806,770 | A | 2/1989 | Hylton et al. |
| 4,932,955 | A | 6/1990 | Merz et al. |
| 4,957,500 | A | 9/1990 | Liang et al. |
| 4,976,721 | A | 12/1990 | Blasnik et al. |
| 5,103,839 | A | 4/1992 | Shichman |
| 5,147,378 | A | 9/1992 | Markham |
| 5,176,700 | A | 1/1993 | Brown et al. |
| 5,250,074 | A | 10/1993 | Wilk et al. |
| 5,275,615 | A | 1/1994 | Rose |
| D346,862 | S | 5/1994 | Koros et al. |
| 5,308,357 | A | 5/1994 | Lichtman |
| 5,385,471 | A * | 1/1995 | Chuen ............... A61C 3/00 294/99.2 |
| 5,478,350 | A | 12/1995 | Kratsch et al. |
| 5,582,617 | A | 12/1996 | Klieman et al. |
| 5,611,813 | A | 3/1997 | Lichtman |
| 5,618,306 | A | 4/1997 | Roth et al. |
| 5,645,552 | A | 7/1997 | Sherts |
| 5,720,751 | A | 2/1998 | Jackson |
| 5,776,147 | A | 7/1998 | Dolendo |
| 5,810,877 | A | 9/1998 | Roth et al. |
| 5,827,263 | A | 10/1998 | Furnish et al. |
| 5,851,214 | A * | 12/1998 | Larsen ............... A61B 17/1608 606/170 |
| 5,921,996 | A | 7/1999 | Sherman |
| 5,944,736 | A | 8/1999 | Taylor et al. |
| 5,980,519 | A | 11/1999 | Hahnen et al. |
| 5,984,934 | A | 11/1999 | Ashby et al. |
| 6,099,539 | A | 8/2000 | Howell et al. |
| 6,117,146 | A | 9/2000 | Slishman |
| 6,206,896 | B1 | 3/2001 | Howell et al. |
| 6,210,419 | B1 | 4/2001 | Mayenberger et al. |
| 6,228,104 | B1 | 5/2001 | Fogarty et al. |
| 6,273,902 | B1 | 8/2001 | Fogarty et al. |
| 6,387,112 | B1 | 5/2002 | Fogarty et al. |
| 6,610,074 | B2 | 8/2003 | Santilli |
| 7,588,585 | B2 | 9/2009 | Gold et al. |
| 8,361,108 | B2 | 1/2013 | Gold et al. |
| 8,506,590 | B2 | 8/2013 | Gold et al. |
| 9,782,174 | B2 | 10/2017 | Gold et al. |
| 2001/0034536 | A1 | 10/2001 | Looper et al. |
| 2009/0093842 | A1 | 4/2009 | Gold et al. |

FOREIGN PATENT DOCUMENTS

| | | |
|---|---|---|
| EP | 0297771 A1 | 1/1989 |
| FR | 2630904 A2 | 11/1989 |
| GB | 2191439 A | 12/1987 |
| NL | 8301618 A | 12/1984 |
| SU | 1123671 A1 | 11/1984 |
| WO | WO-198910095 A1 | 11/1989 |
| WO | WO-199211813 A1 | 7/1992 |
| WO | WO-9720506 A1 | 6/1997 |
| WO | WO-03082129 A2 | 10/2003 |

OTHER PUBLICATIONS

Vertut, Jean and Phillipe Coiffet, Robot Technology: Teleoperation and Robotics Evolution and Development, English translation, Prentice-Hall, Inc. Englewood Cliffs, NJ, USA 1986, vol. 3A, 332 pages.

* cited by examiner

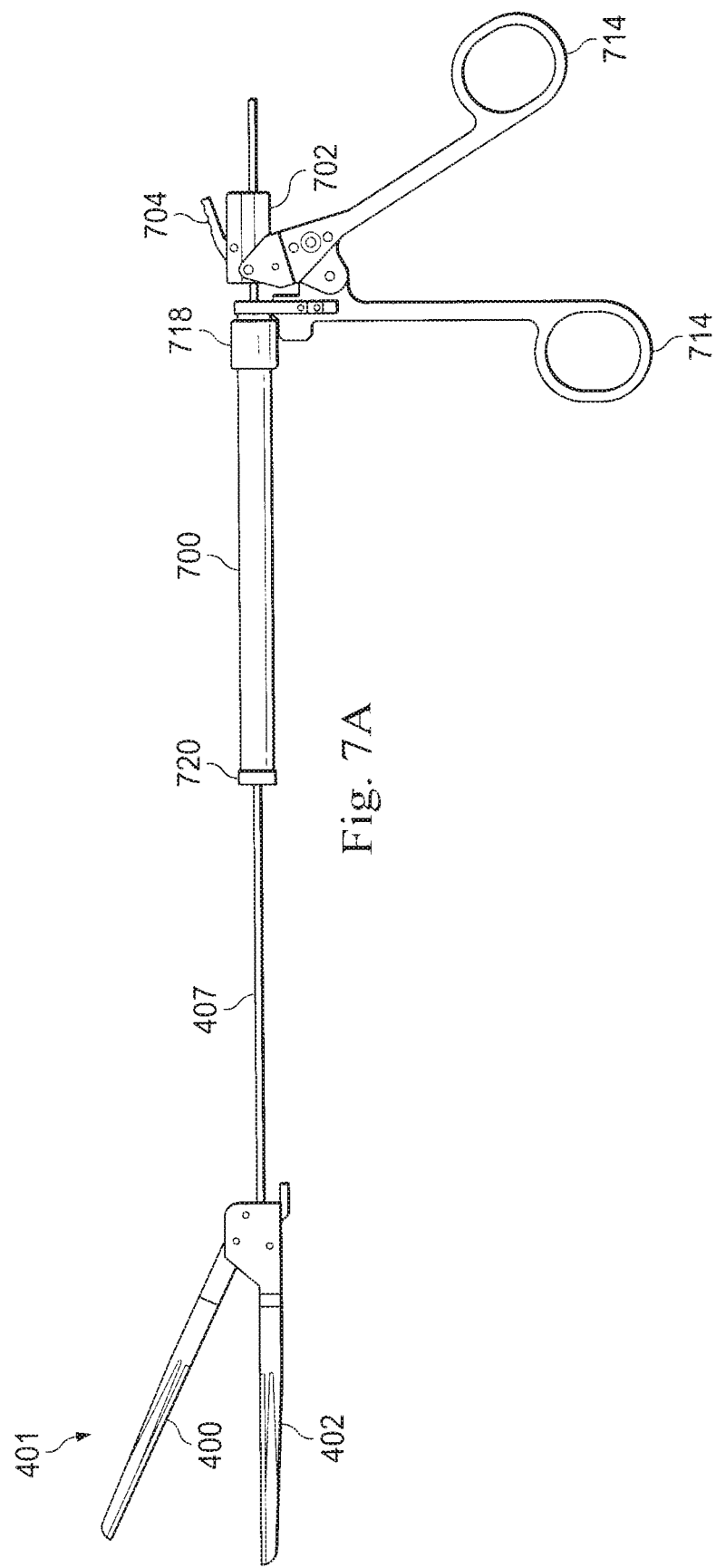

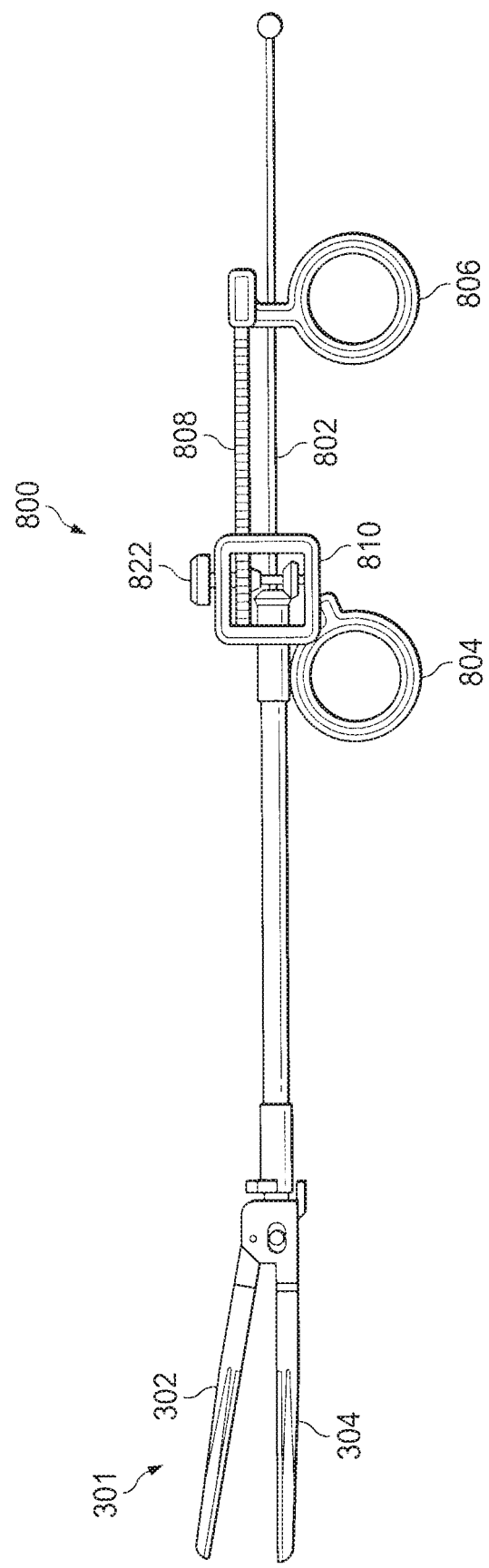

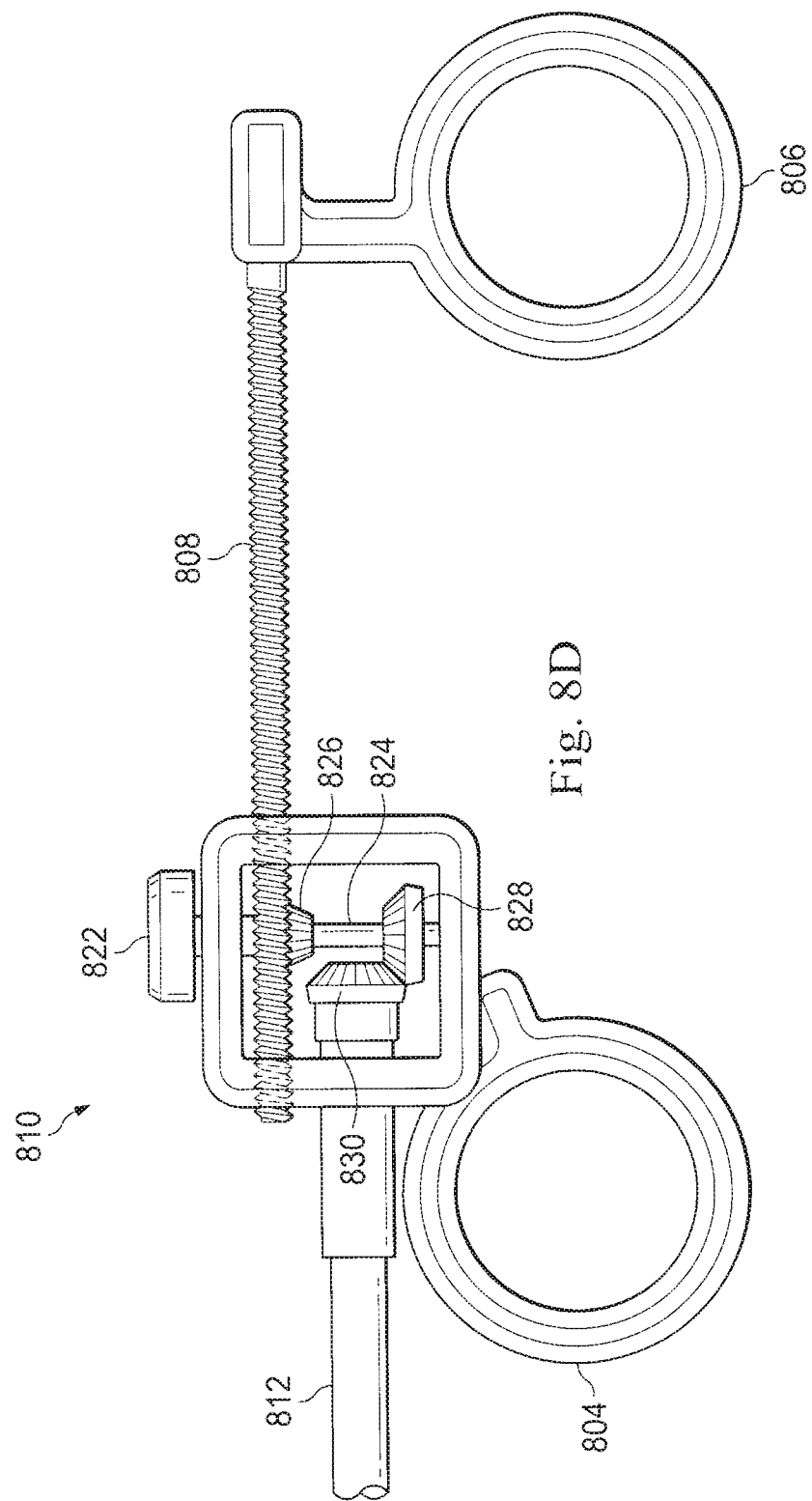

HANDLELESS CLAMPING DEVICE

CROSS-REFERENCE TO RELATED APPLICATIONS

This application is a divisional application of U.S. application Ser. No. 13/942,390 filed on Jul. 15, 2013 (U.S. Pat. No. 9,782,174 issued on Oct. 10, 2017), which is a continuation of U.S. application Ser. No. 12/335,431, filed on Dec. 15, 2008 (U.S. Pat. No. 8,506,590 issued on Aug. 13, 2013), which is a divisional of U.S. application Ser. No. 10/397,915, filed on Mar. 25, 2003, (U.S. Pat. No. 7,588,585 issued on Sep. 15, 2009), which claims priority to U.S. Provisional App. No. 60/368,074 filed on Mar. 26, 2002, the disclosures of which are herein incorporated by reference in their entirety.

FIELD OF THE INVENTION

This invention relates to surgical instruments for occluding and grasping hollow organs as well as grasping solid tissues. Specifically, various clamp devices designed for minimally invasive surgery or for maximizing space in the surgical field are described.

BACKGROUND OF THE INVENTION

Surgical procedures often require retraction, grasping, and the full or partial occlusion of organs such as blood vessels, bile ducts, and intestines, and other various tissues. Traditionally, surgical clamps having pivotable jaws and a handle with a ratchet mechanism are used for this purpose, e.g., Kocher and Kelly clamps. The clamp jaws are actuated by manipulation of the handle at the proximal end of the clamp. However, these clamps are often bulky, and once deployed their handles usually get in the way, obstructing the surgeon's field of view or access to other locations at the surgical site. With the advent of less invasive surgical procedures, surgical sites are becoming smaller and smaller, and obstruction by clamp handles is becoming more problematic. Thus, it would be advantageous to provide a surgical clamp that reduced or even eliminated the bulky handle portion of traditional clamps.

SUMMARY OF INVENTION

The present invention provides various surgical clamps that reside in a surgical field without a bulky handle portion. The surgical clamps generally include first and second body portions that are pivotally connected at their proximal ends. The first and second body portions further include first and second jaw portions extending from the first and second body portions respectively. The clamps include a moveable drive element connected between the first body portion and the second body portion such that movement of the drive element pivotally moves the body portions relative to one another. Movement of the drive element is typically either rotational or translational.

The surgical clamps may be provided with, and releasably attached to, a clamp applier so that the drive element may be actuated from a position distal to the clamp jaw portions. In some instances, the clamp applier slidably engages a clamp along a wire. Once engaged, control arms on the clamp applier may be approximated to actuate the drive element.

In one variation, the drive element includes an orthogonally situated threaded rod and thumbscrew. In another variation, the drive element includes a worm and worm wheel assembly. In a further variation, the drive element is composed of a threaded rod with a mounted nut that is longitudinally aligned with the clamp jaw portions. In yet another variation, the drive element includes a spring-loaded ratchet slide that closes a first jaw portion by proximal movement of the ratchet slide.

BRIEF DESCRIPTION OF THE DRAWINGS

FIGS. 7A-7D show a clamp applier according to another variation of the invention that slides along a wire to engage the surgical clamp of FIG. 4 and actuate its drive element. FIG. 7A is a side view of the clamp and clamp applier disengaged, and the wire upon which the clamp applier slides. FIG. 7B is a cross-sectional view of the clamp applier. FIG. 7C is a perspective view of the clamp applier engaged with the clamp. FIG. 7D is a partial cross-sectional view of the applier engaged with the clamp.

FIGS. 8A-8D illustrate another variation of a clamp applier for translationally actuating a drive element. FIG. 8A shows a perspective view of the clamp and clamp applier disengaged along a wire. FIG. 8B is a side view of the clamp and clamp applier engaged. FIG. 8C is a partial cross-sectional view of the translationally actuated drive element. FIG. 8D is an enlarged side view of the gearbox.

DETAILED DESCRIPTION OF THE INVENTION

The surgical clamp devices of this invention may take various forms, but as further described below, are generally designed to have first and second body portions that are pivotally connected at their proximal ends. The body portions further include first and second jaw portions that extend from the first and second body portions, respectively. Typically, the body portions are pivotally moved by rotational or translational actuation of a drive element. A clamp applier may also be used to deploy the clamp if desired. The surgical clamps of this invention can be used in a variety of open, laparoscopic, or endoscopic procedures, including those requiring occlusion of hollow organs, e.g., blood vessels, ureters, bile ducts, intestines, and the like.

The surgical clamping devices may be made from any biocompatible material including, but not limited to, stainless steel and any of its alloys; titanium alloys, e.g., nickel-titanium alloys; polymers, e.g., polyethylene and copolymers thereof, polyethylene terephthalate or copolymers thereof, nylon, polyurethanes, fluoropolymers, poly (vinylchloride); and combinations thereof.

Surgical Clamps

Figure 1:
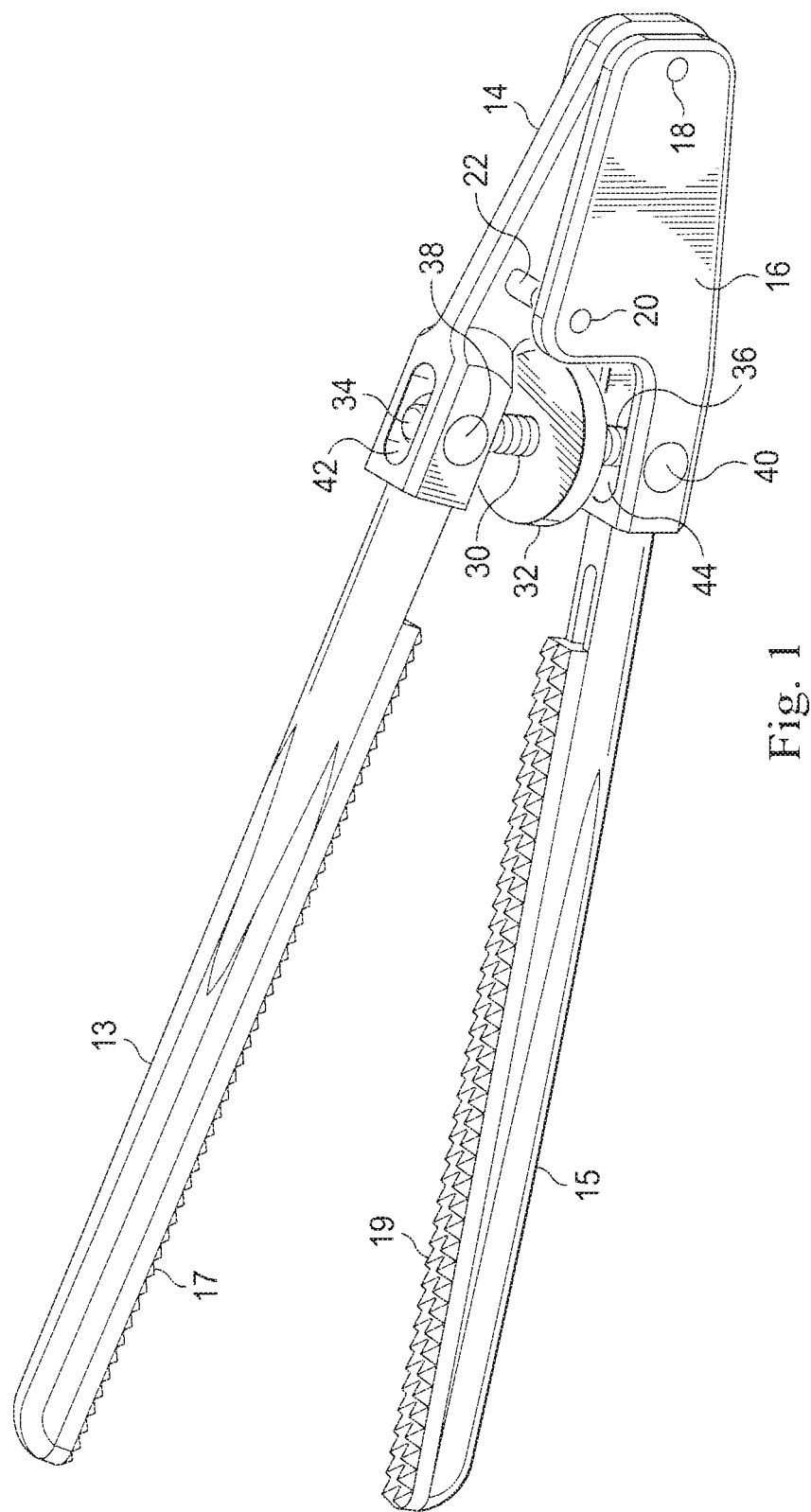
FIG. 1 is a perspective view of a surgical clamp according to one variation of the invention having a drive element situated orthogonal to the jaw portions.

As shown in FIG. 1, the surgical clamps of this invention generally include a first body portion 14 and a second body portion 16. First jaw portion 13 and second jaw portion 15 are connected to, and extend from first body portion 14 and second body portion 16, respectively. Body portions 14 and 16 are linked together by, and pivotable about, pivot 18. Pin 20 of the second body portion 16 is received within slot 22 of the first body portion 14 as a guide for rotation of the body portions about the pivot 18 and to restrict the range of rotational motion about the pivot 18.

Jaw portions 13, 15 and body portions 14, 16 may be sized, shaped, and/or aligned according to their intended use depending on such factors as the hollow organ or solid tissue clamped, surgeon preference, type of procedure involved, and the like. For example, jaw portions 13, 15 may be straight or curved, long or short, or designed such that when directly opposed, they are transversely or vertically aligned with each other. Depending on their material constitution, jaw portions 13, 15 may also be designed to have varying degrees of flexibility and stiffness along their lengths such that they are malleable at their distal ends, and can be shaped by the surgeon just prior to clamp deployment.

In one variation, jaw portions 13, 15 include inserts 17, 19 that cushion a clamped tissue. The inserts 17, 19 may be formed of an elastomer or other like material and can further be textured to improve the grip of the insert on the clamped tissue. The inserts may be affixed to the jaw portions 13, 15 by techniques known in the art, such as those described in U.S. Pat. Nos. 6,099,539 and 6,206,896, each of which is incorporated herein by reference in its entirety. Preferably, the inserts are fixed to the jaw portions using a flexible elongate attachment member configured for receipt in a corresponding channel provided in the jaw portions, such as those described in U.S. Pat. Nos. 6,228,104 and 6,273,902, and U.S. application Ser. No. 09/594,291, each of which is incorporated herein by reference in its entirety.

Drive Elements

A moveable drive element is usually positioned between, and connects, the first and second body portions. The drive element may be configured to be distal or proximal to elements such as pin 20 and slot 22 in the body portions, as shown in FIG. 1. Actuation of the drive element, either by a rotational movement or a translational movement, pivotally moves the body portions, thereby opening or closing the jaw portions. When appropriate, the drive elements are configured to be non-back drivable, e.g., by making a fine pitch between screw threads.

In one variation, provided in FIG. 1, the drive element comprises a threaded rod 30 which is situated orthogonal to the jaw 13, 15 and body 14, 16 portions, and which is integrally connected to a thumbscrew 32 at approximately the midpoint of the rod 30. The rod 30 has a left hand thread on one side of the thumbscrew and a right hand thread on the other side. Rod ends 34, 36 are threaded through nuts 38 and 40 which are disposed within channels 42 and 44 that extend through body portions 14 and 16, respectively. The nuts are mounted within the channels such that they remain aligned with the screw axis when body portions rotate about pivot 18. To actuate the clamp and thereby move the jaw portions either together or apart, the thumbscrew 32 is rotated, which in turn rotates the rod 30. As the rod 30 rotates, it threads through and applies an axial force on the nuts 38, 40, which in turn apply a force onto each body portion 14, 16 and jaw portion 13, 15. The direction of thumbscrew rotation will determine whether the jaws portions open or close. The clamp may also be ergonomically designed to enable the surgeon to hold the clamp in one hand and rotate the thumbscrew with a single digit, e.g., a thumb or forefinger.

Figure 2:
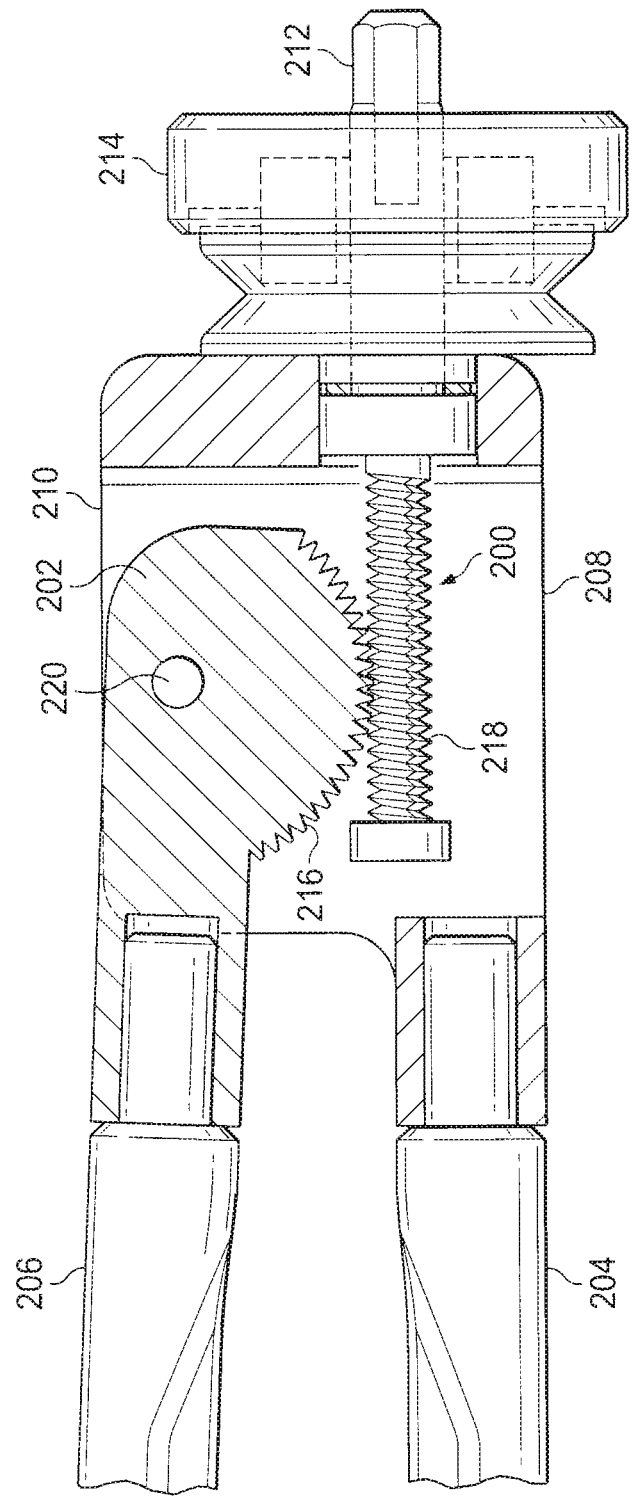
FIG. 2 is a partial cross-sectional view of a surgical clamp according to another variation of the invention having a drive element composed of a worm and worm wheel assembly.

In another variation, as shown in FIG. 2, the drive element includes a worm 200 and worm wheel 202 for actuating the jaw portions 204, 206. In such a variation, first and second body portions 208, 210 are again pivotally connected. The worm 200 is rotatably mounted in the first body portion 208 with an axis of orientation generally parallel to the first jaw portion 204. The worm 200 is connected to a drive shaft 212 which extends proximally from the first body portion 208 and is coupled to an actuating knob 214. The rotational axis of the actuating knob 214 coincides with the drive shaft and worm axis. The worm wheel 202 is typically integrally formed with the second body portion 210 and includes gear teeth 216 arranged in an arc about the pivot 220 that couples the first and second body portions 208, 210 together. Gear teeth 218 on the worm 200 mesh with the gear teeth 216 of the worm wheel 202. Rotation of the actuating knob 214 turns the drive shaft 212, which in turn rotates the worm 200. Rotation of the worm 200 drives the worm wheel 202 and causes movement of the second body portion 210 about the pivot 220, thus moving the second jaw 206 toward or away from the first jaw 204, depending on the direction of rotation of the worm 200.

Figure 3:
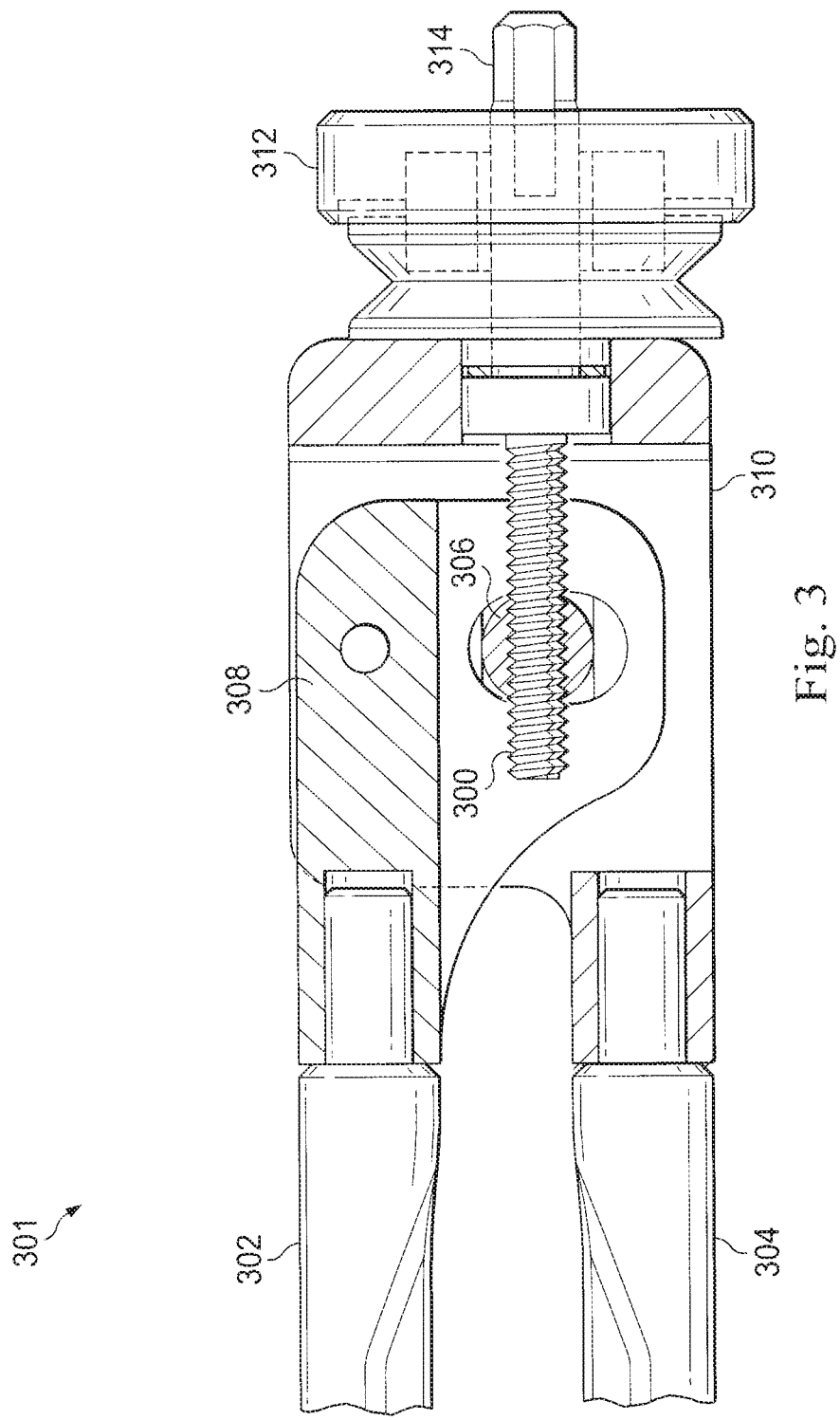
FIG. 3 is a partial cross-sectional view of a surgical clamp according to another variation of the invention having a drive element actuated by rotation of a threaded rod through a nut.

In a further variation, shown in FIG. 3, the drive element of clamp 301 includes a threaded rod 300 which is axially aligned with the first and second jaw portions 302, 304 when they are in the clamped position. The rod 300 is connected to a drive shaft 314 which extends proximally from the drive element. The drive shaft 314 couples an actuating knob 312 mounted on the drive shaft 314 to the rod 300. The rod 300 is threaded through a nut 306 which is disposed between the first and second body portions 308, 310. To actuate the drive element and open or close the jaw portions 302, 304, the actuating knob 312 is rotated, which in turn rotates threaded rod 300. As rod 300 rotates, it threads through and applies an axial force on the nut 306, which in turn applies a force onto body portions 308, 310. The direction of rotation of the actuating knob 312 determines whether the jaw portions 302, 304 open or close.

Figure 4:
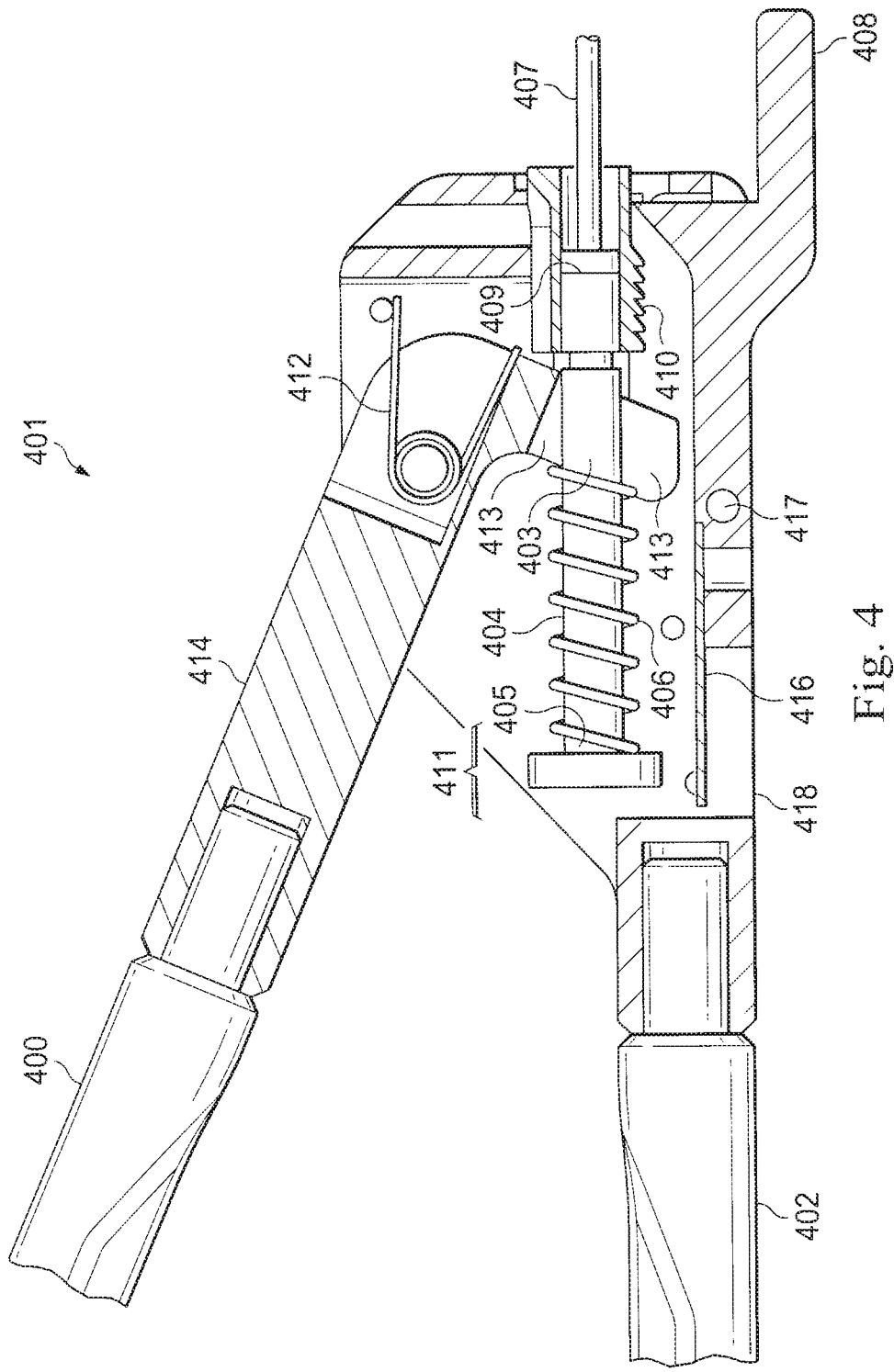
FIG. 4 is a partial cross-sectional view of a surgical clamp according to another variation of the invention having a translationally actuated drive element.

In yet a further variation, the drive element includes a spring loaded ratchet slide. As shown in FIG. 4, the drive element of clamp 401 is axially aligned with the first and second jaw portions 400, 402 when the jaws are in the clamped position, and is actuated by proximal movement of a ratchet slide 404. A spring 406 having a distal end 405 and a proximal end 403 is concentrically mounted on the ratchet slide 404 and fixedly attached to the distal end 411 of the ratchet slide 404 at its distal end 405. The proximal spring end 403 is free to slide along the ratchet slide 404 and engage the engaging arm 413 of the first body portion 414 when the ratchet slide 404 is moved proximally. One way to move the ratchet slide 404 is by applying an axial force to a wire 407 attached to the proximal end 409 of the ratchet slide. When the wire is moved proximally, the ratchet slide 404 is also moved proximally, and the proximal end 403 of the spring 406 engages and compresses itself against engaging arm 413, exerting a force on the first body and first jaw portion 400, to thereby bring the first jaw portion 400 together with the second jaw portion 402. The spring 406 also serves to increase the clamping force resolution. Another spring 412 may be coupled to the first body portion 414 to aid in movement of the first jaw portion 400. A pawl 408 keeps the jaw portions 400, 402 closed. The pawl 408 rotates with respect to a pin 417 which is connected to the second body portion 418. To release the pawl 408 and open the jaw portions 400, 402, a generally rotational force sufficient to counter the force supplied by a leaf spring 416 is applied to the pawl 408 to disengage it from the ratcheted portion 410 of the ratchet slide.

Clamp Appliers

As will be appreciated, it may be desirable to deploy the surgical clamps of this invention using a clamp applier, e.g., when the surgical field or access to an organ or tissue is limited. The clamp appliers are generally releasably attached to one or more applier areas on the surgical clamps, e.g., the actuating knob, the drive shaft, the first body portion, and/or the second body portion, and may employ a rotational or translational movement to actuate the drive elements, but in all instances, actuate drive elements from a position distal to the first and second jaw portions.

Figure 5:
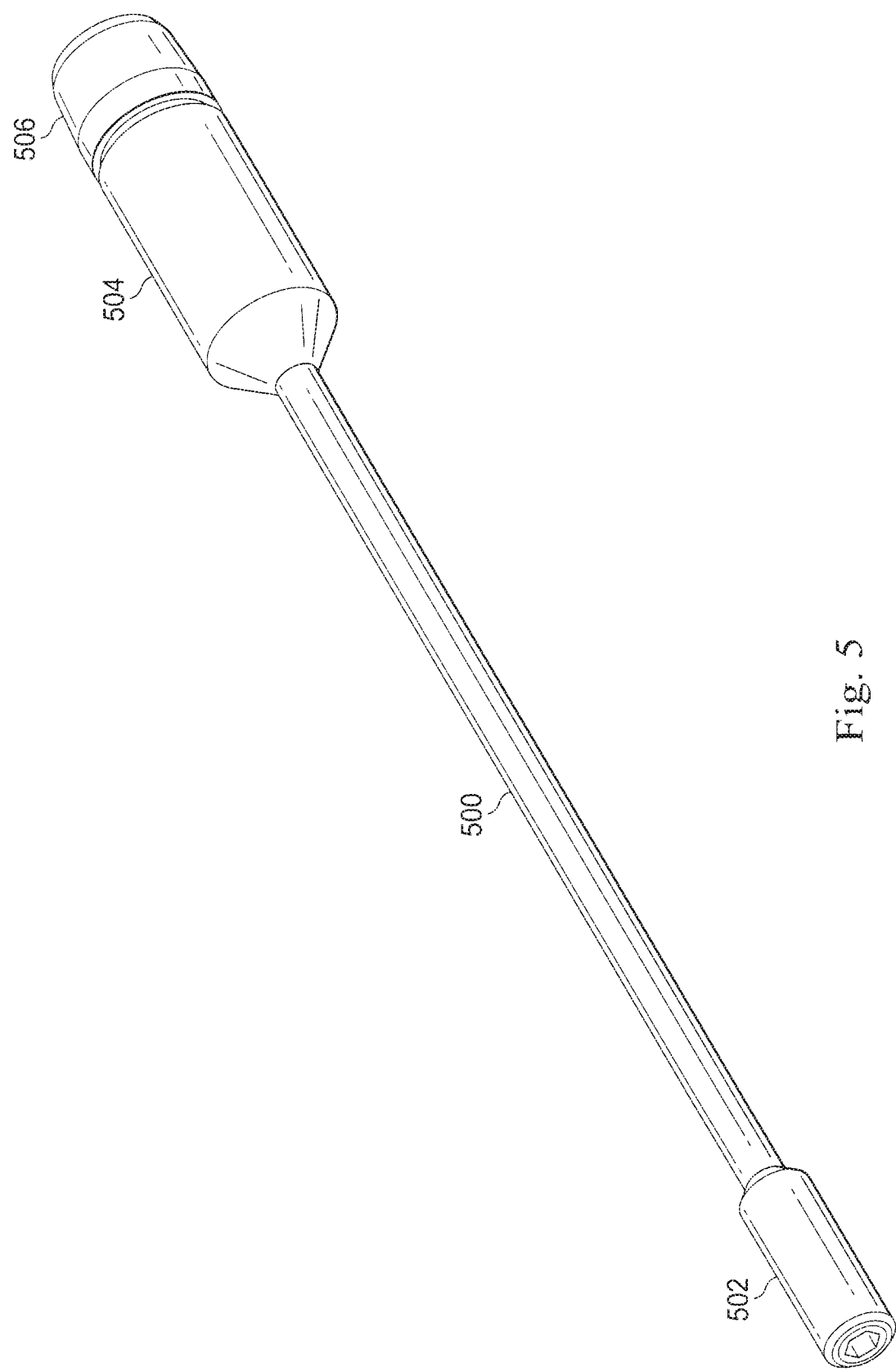
FIG. 5 is a perspective view of a clamp applier according to one variation of the invention.

In one variation, as shown in FIG. 5, a clamp applier configured for use with a surgical clamp having a worm and worm wheel assembly (FIG. 2) or a longitudinally aligned threaded rod and nut (FIG. 3) is provided. The clamp applier includes a rotating shaft 500 that terminates at its distal end in a drive head 502 configured for receipt of a drive element, e.g., a clamp actuating knob (element 312 in FIG. 3) or a drive shaft (element 212 in FIG. 2). When secured to such an element as a clamp actuating knob 214, 312, the clamp applier may be aligned along the rotational axis of the knob or within about 15 degrees, within about 30 degrees, or within about 45 degrees of the rotational axis of the knob. The proximal end of the rotating shaft 500 includes a handle 504 and a handle actuating knob 506 distal to the handle 504. The handle actuating knob 506 is connected to the rotating shaft 500 at its proximal end such that rotation of the knob 506 rotates the shaft 500. In use, the drive head 502 of the rotating shaft 500 is releasably attached to, e.g., a clamp actuating knob. The handle actuating knob 506 is manually rotated relative to the handle, which in turn rotates the clamp actuating knob 214, 312 to actuate the clamp jaws portions 204, 206, 302, 304 as described above. Or, if the drive head 502, the rotating shaft 500, and the handle 504 are fixedly connected, and the actuating knob is rotatably connected to the handle 504, the drive element may be actuated by holding the actuating knob 506 stationary and rotating as a single unit, the handle 504, rotating shaft 500, and drive head 502 relative to the actuating knob 506. A bracket assembly (not shown), being fixedly connected to the handle, may be used to restrain the body portions of the clamp from rotating if desired. The handle 504 and handle actuating knob 506 may also be variously shaped and sized depending, e.g., on the method of clamp deployment, surgeon preference, or type of procedure.

Figure 6:
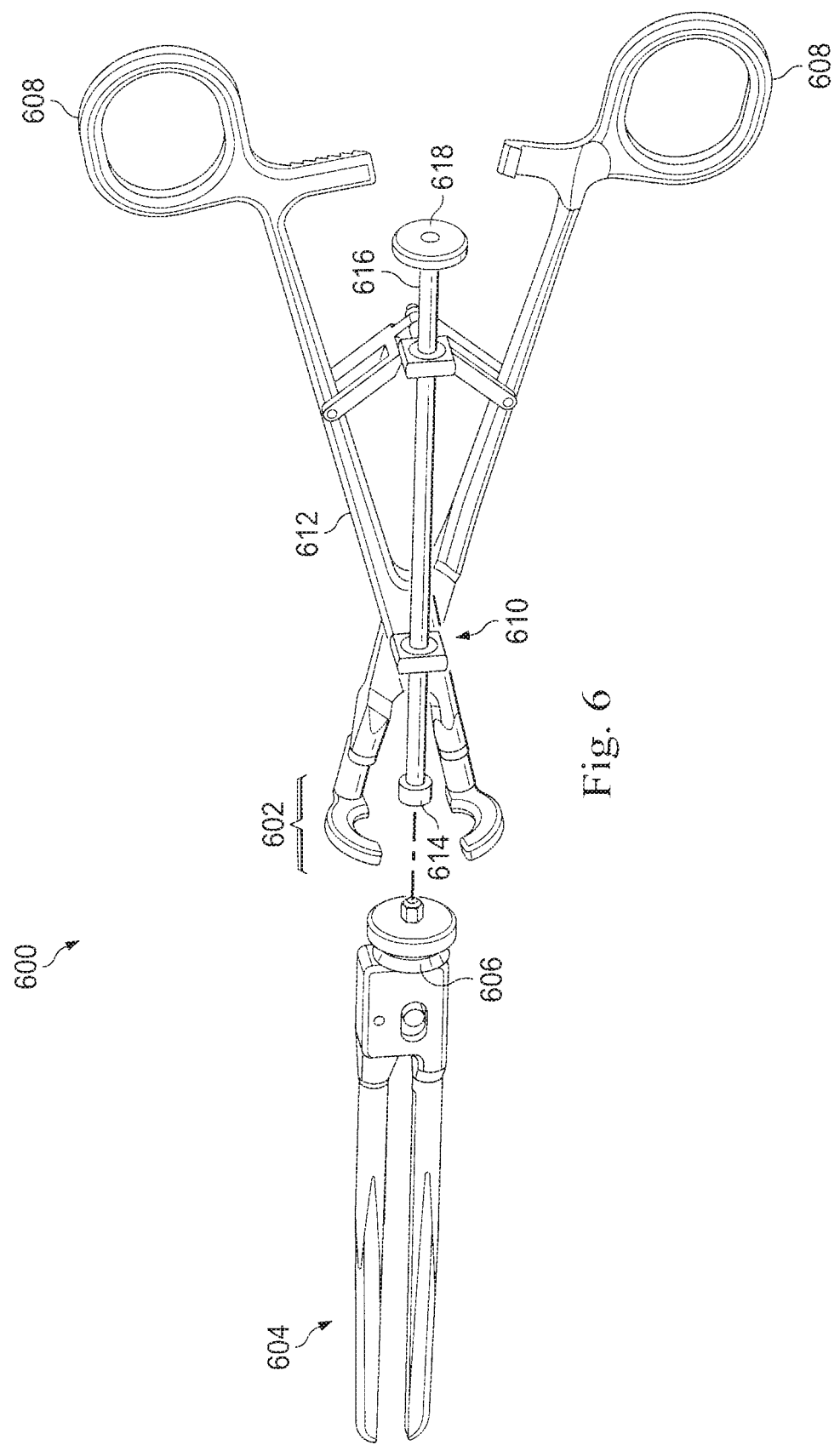
FIG. 6 is a perspective view of another clamp applier according to another variation of the invention disengaged from the clamp in FIG. 3 having a rotationally actuated drive element.
Figure 7B:
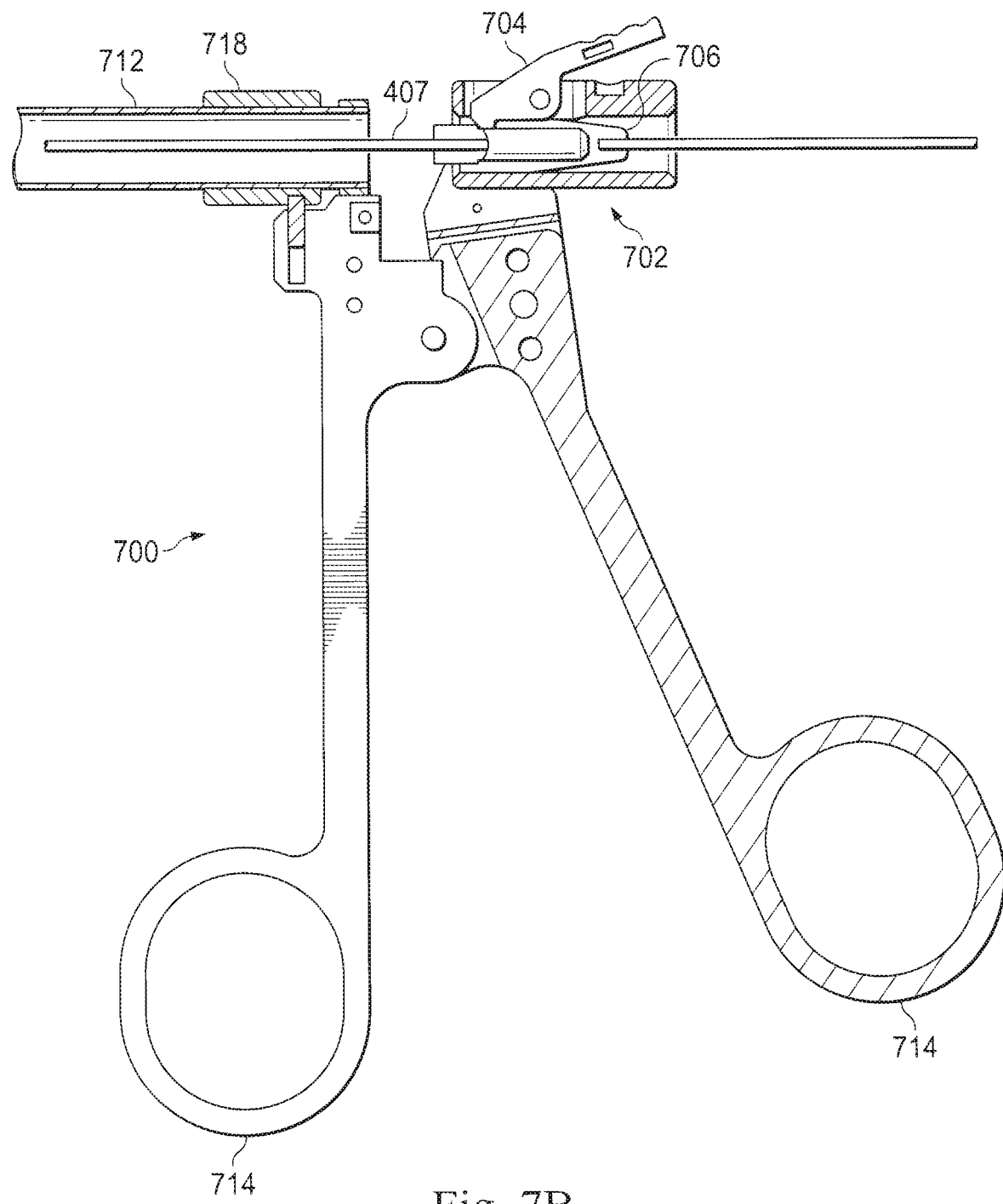
Figure 7C:
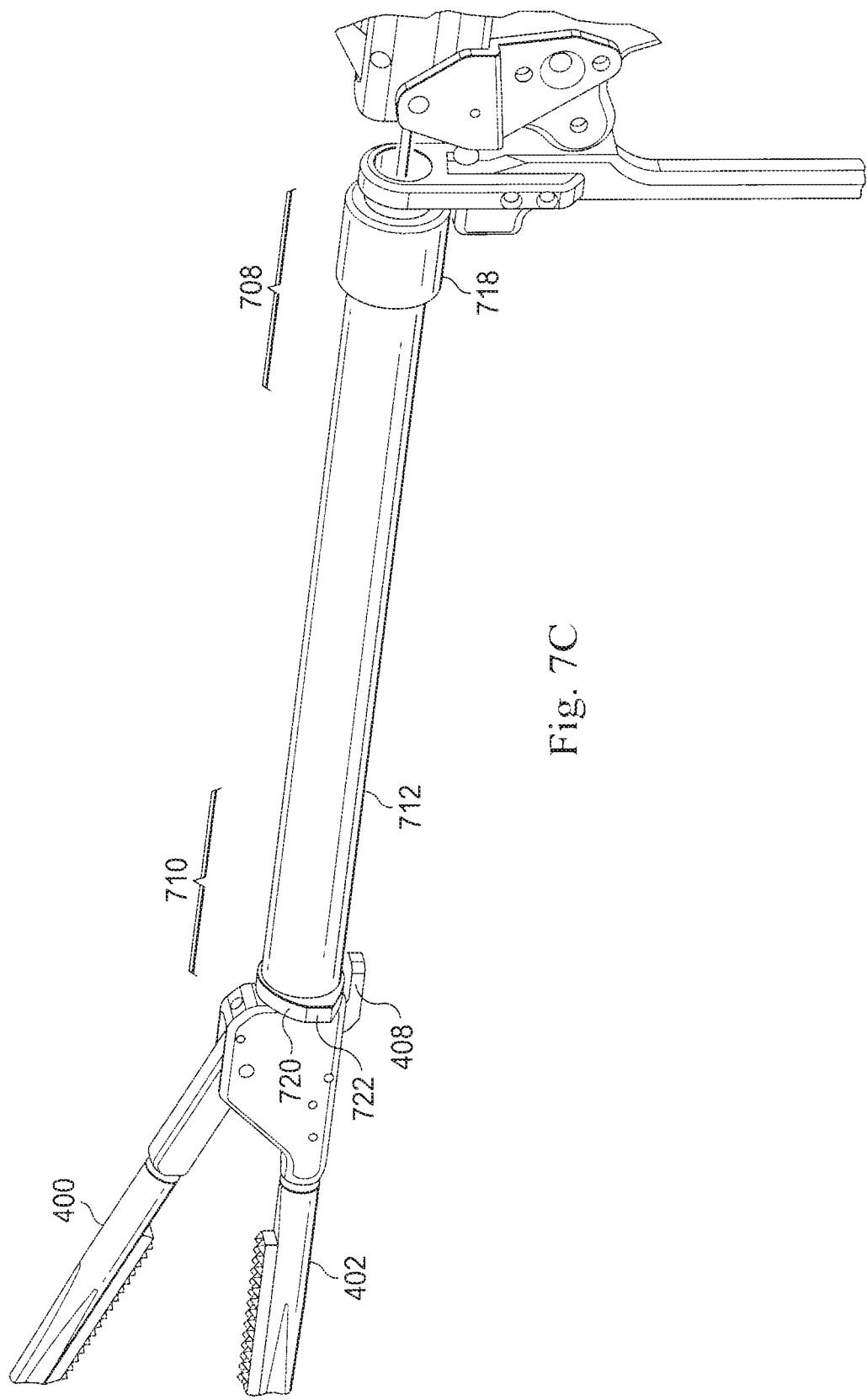
Figure 7D:
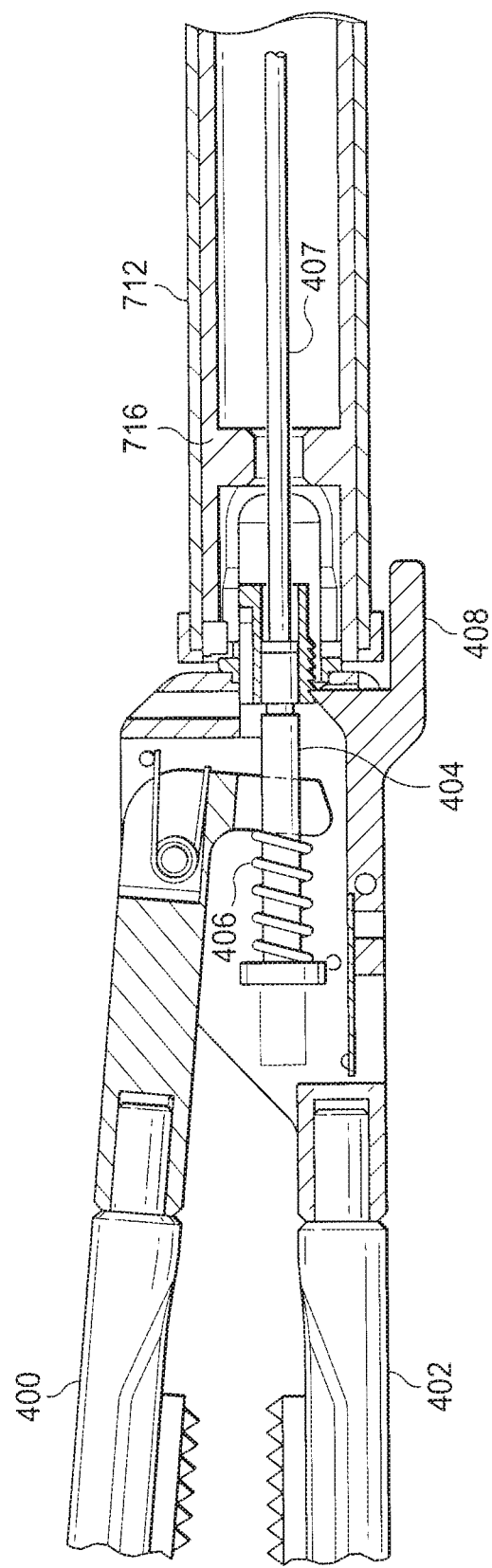

FIG. 6 shows another variation of a clamp applier. In this variation, the distal portion 602 of clamp applier 600 is sized and shaped to grasp an applier area of surgical clamp 604. For example, distal portion 602 is shown to be curved in FIG. 6 so that it may grasp clamp 604 along its cylindrical V-groove 606 when control arms 608 are approximated (to bring them together). Once releasably attached to clamp 604, the clamp 604 may be positioned, e.g., from a location distal to the surgical field. A component 610 similar to the clamp applier in FIG. 5 is coupled to the body 612 of the clamp applier 600. The component 610 includes a drive head 614, a rotating shaft 616, and an actuating knob 618, typically fixedly connected. The component 610 is coupled to the body 612 of the clamp applier 600 at least at one position along the rotating shaft 616. In use, after clamp 604 has been positioned, the drive head 614 releasably engages any part of a rotationally actuated drive element, e.g., the drive shaft (212) in FIG. 2. Rotation of the actuating knob 618 rotates the rotating shaft 616 and drive head 614, which thereby rotates the drive element.

The clamp applier may also slide along a wire secured to the clamp to releasably attach itself to the clamp. The clamp appliers in these instances include control arms that are approximated to actuate the drive element. In one variation, as shown in FIGS. 7A-7D, the clamp applier 700 includes a handle attachment 702, a spring-loaded rear snap 704, an outer tube 712, an inner tube 716, a rotator knob 718 concentrically mounted on the proximal end 708 of the outer tube, and a release disc 720 having raised areas 722 concentrically mounted on the distal end 710 of the outer tube. The clamp applier 700 may be configured for use with clamps having drive elements as described in FIG. 4. When wire fitting 706 engages the spring-loaded rear snap 704, the clamp applier 700 is releasably attached to the clamp 401. Pressing down on the rear snap 704 and pulling the clamp applier 700 away from the clamp 401 then disengages the applier 700 from the clamp 401. For example, as provided in FIG. 7D, a wire 407 coupled to the ratchet slide 404 is placed under tension and moved proximally as the pair of control arms 714 are squeezed together. Proximal movement of the ratchet slide 404 exerts a compressive force on a spring 406 concentrically mounted on the ratchet slide 404 to exert a force on a first jaw portion 400 to bring it together with the second jaw portion 402. The spring-loaded pawl 408 works to prevent the jaw portions from opening as described above. To release the pawl 408, the rotator knob 718 is rotated, which in turn rotates the outer tube 712 and release disc 720 on the outer tube 712. Rotation of the release disc 720 thereby causes the raised areas 722 on the release disc 720 to exert a downward and rotational force on the pawl 408 to release it.

Figure 8A:
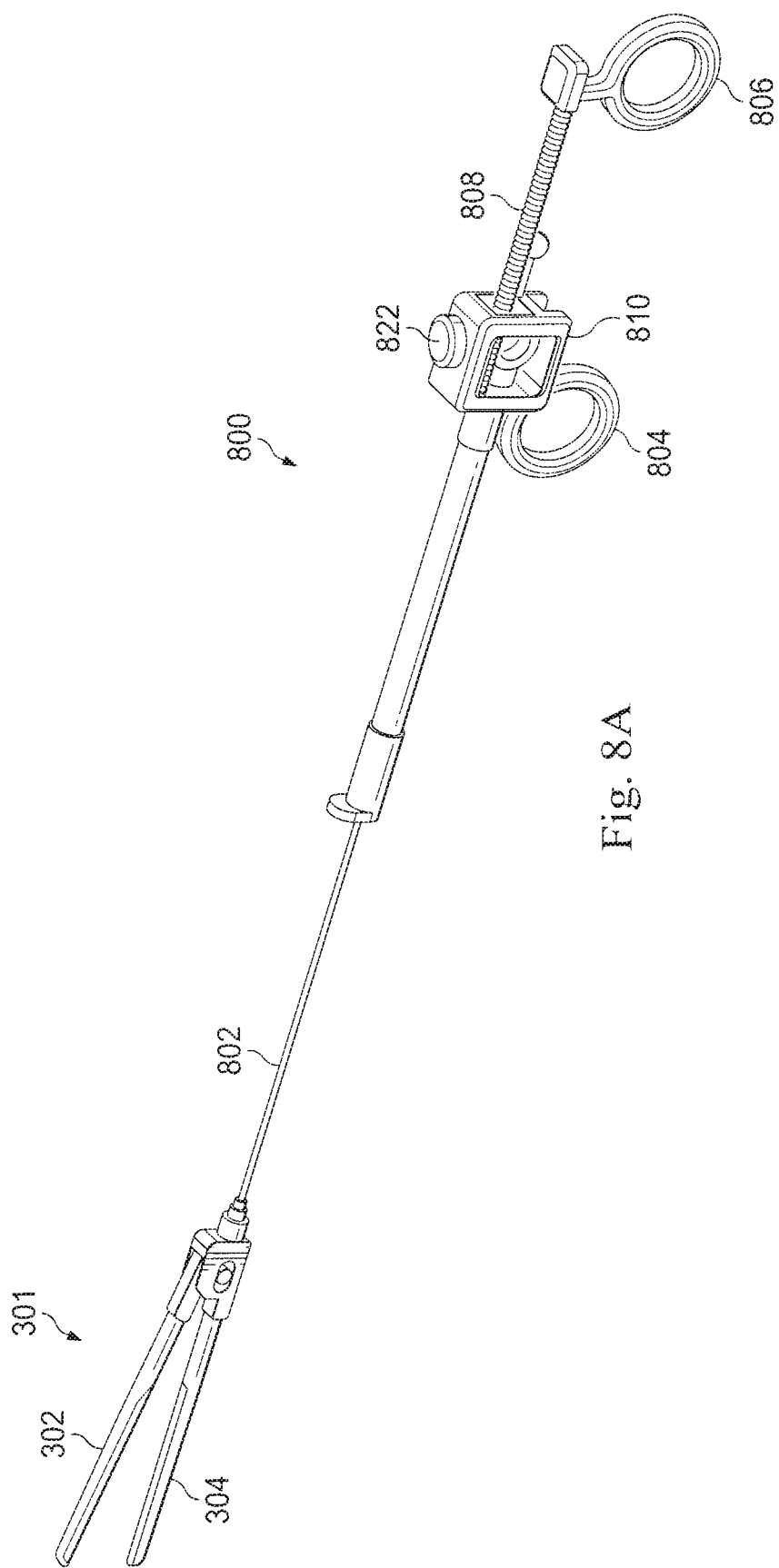
Figure 8C:
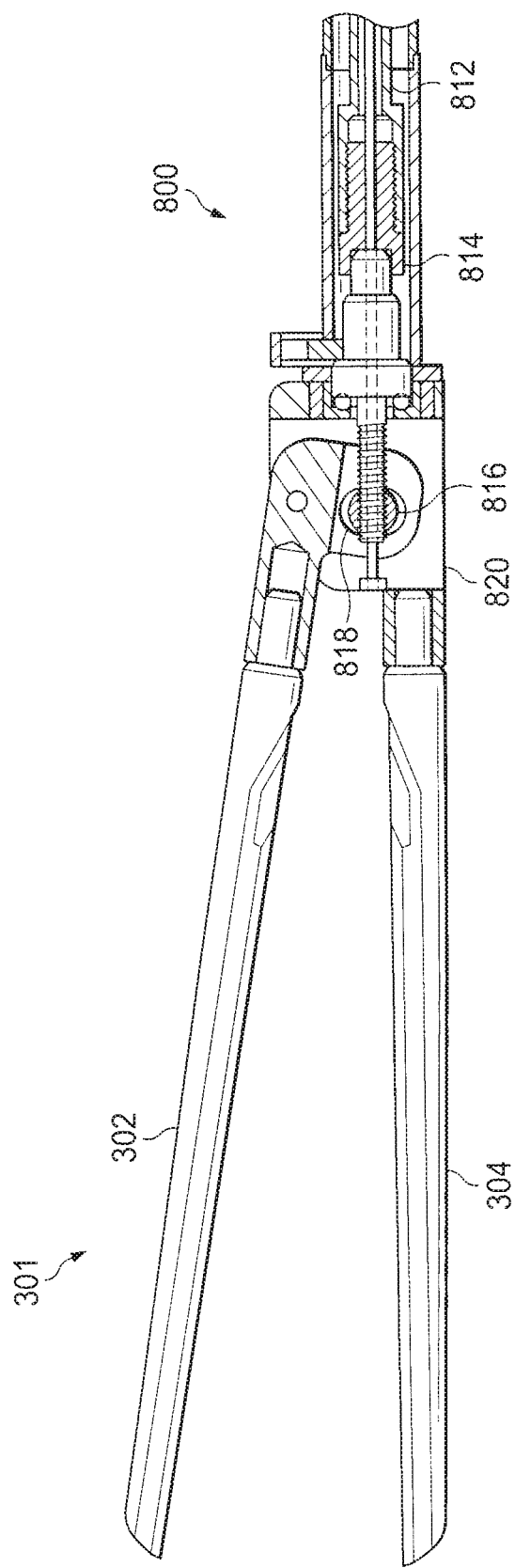

Another variation, particularly useful with a clamp such as shown in FIG. 3, is provided in FIGS. 8A-8D. In this variation, the clamp applier 800 is also slid along a wire 802 to releasably attach to the clamp 301. The front and rear control arms 804 and 806, respectively, of the clamp applier 800 are then also squeezed together to actuate the drive element of the clamp 301, but they are translationally approximated instead of rotationally approximated. As shown in FIG. 8B, after slidably engaging the clamp 301, the clamp jaw portions 302, 304 are closed by translationally approximating control arms 804, 806. The linear motion of a rack 808 on the rear control arm 806 through a gearbox 810 causes rotation of an inner shaft 812 of the clamp applier 800 and rotation of a screw head 814 connected to the inner shaft 812. This in turn exerts a force on a nut 816, which exerts a force on the first jaw portion 302, causing it to close. A slot 818 in the second body portion 820 constrains the nut 816 to only move horizontally. Gearbox 810 is shown in greater detail in FIG. 8D, and generally includes a gear shaft 824, a pinion gear 826, a first bevel gear 828, and a second bevel gear 830. The pinion gear 826 and first bevel gear 828 are connected to gear shaft 824. The second bevel gear 830 is connected to inner shaft 812. Pinion gear 826, first and second bevel gears 828, 830, and rack 808 have teeth. The teeth of the first and second bevel gears contact each other, and the teeth of the pinion gear 826 and rack 808 contact each other. Linear movement of the rack 808 to approximate the control arms 804, 806 rotates the pinion gear 826 which rotates the gear shaft 824 and first bevel gear 828, which rotates the second bevel gear 830 and the inner shaft 812 connected to the second bevel gear 830 to actuate the drive element. Pulling the rear control arm 806 away from the front control arm 804 opens the first and second jaw portions 302, 304. A spring-loaded release button 822 is axially fixed to the gear shaft 830 but is free to rotate about the gear shaft axis. The release button 822 may be pressed to temporarily disengage the gears in the gearbox 810, allowing the user to slide the rear control arm 806 to a different position without actuating the jaw portions.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

What is claimed is:

1. A method of operating a medical device comprising a first jaw portion and a second jaw portion, the method comprising:
    rotating a first rotating element about a rotational axis of the first rotating element to cause rotation of a second rotating element about a rotational axis of the second rotating element; and
    restricting a range of rotational motion of the first and second jaw portions, wherein the range of rotational motion is restricted by an elongate slot of a first body portion and a pin affixed to a second body portion, wherein the first jaw portion is coupled to the second jaw portion by the first body portion and the second body portion,
    wherein the rotation of the second rotating element causes translation of a first actuation element along the rotational axis of the second rotating element,
    wherein the translation of the first actuation element causes pivotal motion of the first jaw portion towards the second jaw portion, wherein the pivotal motion occurs about a single pivot pin, and
    wherein the elongate slot of the first body portion and the pin affixed to the second body portion are positioned between the second rotating element and the single pivot pin.

2. The method of claim 1, wherein the first actuation element further comprises an inner surface configured to contact an outer surface of the second rotating element,
    wherein the rotation of the second rotating element causes the outer surface of the second rotating element to apply a first force to the inner surface of the first actuation element, the first force causing the translation of the first actuation element, and
    wherein the first force further causes the first actuation element to apply a second force to the first body portion, the second force causing the pivotal motion of the first jaw portion towards the second jaw portion.

3. The method of claim 2, wherein the first actuation element is threadedly coupled to the second rotating element, and wherein the first actuation element comprises an outer surface slidably coupled to an inner surface of the first body portion.

4. The method of claim 1, wherein the second jaw portion remains fixedly positioned relative to the rotational axis of the second rotating element.

5. The method of claim 1, wherein the first body portion defines a first opening, and wherein the rotation of the second rotating element comprises rotating a portion of the second rotating element within the first opening.

6. The method of claim 1, wherein the first jaw portion and the second jaw portion are coupled together to pivot about the single pivot pin.

7. The method of claim 6,
    wherein restricting the range of rotational motion of the first and second jaw portions includes extending the pin affixed to the second body portion through the elongate slot of the first body portion.

8. The method of claim 1, further comprising:
    coupling a first textured member to the first jaw portion; and
    coupling a second textured member to the second jaw portion,
    wherein the first textured member protrudes from the first jaw portion toward the second textured member, and wherein the second textured member protrudes from the second jaw portion toward the first textured member.

9. The method of claim 1, wherein when the first and second jaw portions are in an open configuration, a proximal portion of the first body portion is received by a proximal portion of the second body portion in a slot formed in the second body portion.

10. The method of claim 9, wherein when the first and second jaw portions are in a closed configuration, the proximal portion of the first body portion and a distal portion of the first body portion are received in the slot.

11. A method of operating a medical device comprising a first jaw portion and a second jaw portion, the method comprising:
    rotating a threaded rotating element about a rotational axis of the threaded rotating element, wherein the threaded rotating element is coupled to a first body portion of the medical device by a first threaded coupling element, and wherein the threaded rotating element is coupled to a second body portion of the medical device by a second threaded coupling element; and
    restricting a range of rotational motion of the first and second jaw portions, wherein the range of rotational motion is restricted by an elongate slot of the first body portion and a pin affixed to the second body portion, wherein the first jaw portion is coupled to the second jaw portion by the first body portion and the second body portion,
    wherein the rotating the threaded rotating element about the rotational axis of the threaded rotating element translates the first threaded coupling element that is rotatably disposed within a channel of the first body portion,
    wherein the translation of the first threaded coupling element pivotally actuates the first jaw portion towards the second jaw portion, wherein the pivotally actuating the first jaw portion towards the second jaw portion includes pivotally actuating the first body portion towards the second body portion about a single pivot pin, and
    wherein the elongate slot of the first body portion and the pin affixed to the second body portion are positioned between the threaded rotating element and the single pivot pin.

12. The method of claim 11, further comprising:
    maintaining, by the first threaded coupling element, axial alignment with the rotational axis of the threaded rotating element as the first and second jaw portions pivotally actuate.

13. The method of claim 11,
wherein a threaded disc is coupled to the threaded rotating element, and wherein the threaded disc extends laterally beyond the first body portion and the second body portion.

14. The method of claim 13, wherein the threaded disc is positioned between the first body portion and the second body portion.

15. The method of claim 13, wherein a portion of the threaded disc extends between the first jaw portion and the second jaw portion.

16. The method of claim 11,
wherein the pin affixed to the second body portion is at least partially extended through the second body portion.

17. The method of claim 11,
wherein a proximal portion of the first body portion is received by the second body portion in a slot formed in the second body portion.

18. The method of claim 11, wherein the first body portion is coupled to the second body portion by the single pivot pin.

19. The method of claim 11, wherein restricting a range of rotational motion of the first and second jaw portions includes extending the pin affixed to the second body portion through the elongate slot of the first body portion.

20. The method of claim 11, wherein when the first and second jaw portions are in a closed configuration, a proximal portion and a distal portion of the first body portion are received by the second body portion in a slot formed in the second body portion.

\* \* \* \* \*